United States Patent [19]

Tsau

[11] 4,448,716

[45] May 15, 1984

[54] DIPEPTIDE SWEETENER-METAL COMPLEXES

[75] Inventor: Josef H. Tsau, Prospect Heights, Ill.

[73] Assignee: G. D. Searle & Co., Skokie, Ill.

[21] Appl. No.: 354,574

[22] Filed: Mar. 4, 1982

[51] Int. Cl.$^3$ .................... C07C 103/52; A23L 1/236
[52] U.S. Cl. ........................... 260/112.5 R; 426/548; 426/271
[58] Field of Search ................ 260/112.5 R; 424/177; 426/548, 271

[56] References Cited

U.S. PATENT DOCUMENTS 4,029,701  6/1977  Haas et al. ................... 260/112.5 R

OTHER PUBLICATIONS

Thomas E. Furia, Food Technology, Geigy Chemical Corporation, N.Y., Dec. (1964), pp. 1-10.
MacDonald, *J. Med. Chem.*, vol. 23, 413-420 (1980).
Kawai, *J. Med. Chem.*, vol. 23, No. 4, 420-424 (1980).
The Merck Index, Ninth Ed., Merck and Co., Inc., Rahway, N.J., p. 523.

*Primary Examiner*—Delbert R. Phillips
*Assistant Examiner*—F. T. Moezie
*Attorney, Agent, or Firm*—John J. McDonnell; Steven M. Odre

[57] ABSTRACT

The invention relates to metal complexes of dipeptide sweeteners, such as L-aspartyl-L-phenylalanine methyl ester, with improved dissolution rate, solubility and stability.

21 Claims, No Drawings

DIPEPTIDE SWEETENER-METAL COMPLEXES

BACKGROUND OF THE INVENTION

1. Field of Invention

This invention relates to novel sweeteners. In particular, the invention relates to metal complexes of dipeptide sweeteners which show improved dissolution rate, solubility and temperature stability without significant loss of sweetness.

It has been found that certain dipeptide compounds possess an intense sweetness. Examples of these compounds are set forth in U.S. Pat. Nos. 3,475,403 issued Oct. 28, 1969, 3,492,131 issued Jan. 27, 1970, and in the following foreign patents; Republic of South Africa Pat. Nos. 695,083 published July 12, 1969, 695,910 published Aug. 14, 1969 and German Pat. No. 2,054,545 published May 19, 1971. Generically, these compounds are represented by the formula:

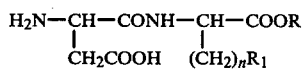

wherein R represents the lower alkyls, lower alkyaryls and cycloalkyls, n stands for integers 0 through 5, $R_1$, represents (a) phenyl group, (b) lower alkyls, (c) cycloalkyls, (d) $R_2$ where $R_2$ is hydroxy, lower alkoxy, lower alkyl, halogen, (e) $S(O)_m$(lower alkyl) where m is 0, 1 or 2 and provided n is 1 or 2, (f) $R_3$ where $R_3$ represents an hydroxy or alkoxy and (g) single or double unsaturated cycloalkyls with up to eight carbons. Most suitable among these compounds are the lower alkyl esters of aspartyl phenylalanine (U.S. Pat. No. 3,492,131) wherein the stereochemical configuration is DL-L, L-L, DL-DL, or L-DL. Illustrative of the lower alkyl esters are methyl, ethyl, propyl, butyl, pentyl, hexyl, heptyl and the branched chain groups isomeric therewith, with the methyl ester being the most preferred embodiments, said patents which are herein incorporated by reference.

These dipeptides of Formula I have significant sweetening properties. Problems have arisen, however, with the use of these compounds in dry systems in that their rate of solution into aqueous medium is markedly slower than sucrose, the absolute solubility is poor and the compounds readily decompose above 80° C. as exemplified by the methyl ester of L-aspartyl-L-phenylalanine (APM).

2. Description of the Prior Art

Dipeptide sweeteners are well known in the art as described above. While the problem of stability, dissolution rate and solubility are well documented, little has been done to overcome the problem. In U.S. Pat. No. 4,139,639 a chewing gum composition is described in which APM is fixed in gum Arabic and/or the reaction product of a compound containing a polyvalent metallic ion, with an ungelatinized starch acid-ester of a substituted dicarboxylic acid thus forming an encapsulated APM-gum composition which increases the stability of the APM. In addition, U.S. Pat. No. 4,029,701 describes the hydrohalide salts of dipeptide sweeteners as being an improvement in terms of the rate of dissolution. But the hydrochloride salts do not exhibit heat stability or appreciable increases in solubility. Glickman, in U.S. Pat. No. 3,761,288 describes a method for spray drying aspartame which increases the solubility of aspartame and enables aspartame to be spray dryed at 100° C. or above without appreciable decomposition but only if the contact time is short as in normal spray drying techniques.

SUMMARY OF THE INVENTION

The invention relates to a dipeptide metal complex sweetener of the formula:

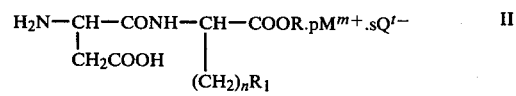

wherein the stereochemical configuration is:

DL-DL, DL-L, L-DL, or L-L;

wherein R is:
(a) alkyl of from one to six carbon atoms, inclusive;
(b) alkylaryl, the alkyl portion of from one to six carbon atoms, inclusive, the aryl portion of from six to ten carbon atoms inclusive; or
(c) cycloalkyl of from three to seven carbon atoms inclusive;

wherein n is an integer of from 0 to 5;

wherein $R_1$ is:
(a) alkyl of one to six carbon atoms, inclusive; or
(b) a saturated, unsaturated, or partially saturated 6 carbon ring, which may be optionally unsubstituted or substituted at the 4 position by $R_2$.

wherein $R_2$ is:
(a) hydroxy;
(b) alkoxy of one to six carbon atoms, inclusive;
(c) alkyl of one to six carbon atoms, inclusive;
(d) halogen; or
(e) $S(O)_f(CH_2)_k(CH_3)$ wherein f is 0, 1, or 2, wherein k is an integer of from 0 to 5, with the proviso that n is 1 or 2;

wherein m and t are integers of from one to three, either the same or different;

wherein p is the ratio of $M^{m+}$ to the dipeptide sweetener which may be from 0.1 to 3;

wherein s is the ratio of $Q^{t-}$ to the dipeptide sweetener and wherein $p \times m = s \times t$;

wherein $M^{m+}$ is a pharmacologically acceptable Metal ion or a combination of pharmacologically acceptable Metal ions;

wherein $Q^{t-}$ is a pharmacologically acceptable anion or a combination of pharmacologically acceptable anions;

wherein the dipeptide sweetener-metal complex may either be hydrated or unhydrated.

In addition, the invention relates to a liquid low calorie sweetener can be produced comprising the above low-calorie sweetener complex which is dissolved in a suitable solvent or combination of solvents, in an amount effective to make a high concentration liquid low-calorie sweetener.

The invention also relates to a dipeptide sweetener-metal complex mixed with an amount of a pharmacologically acceptable strong chelating agent which can be used in alkaline pH beverages, or dairy product solutions.

Examples of alkyl of from one to six carbon atoms, inclusive are methyl, ethyl, propyl, butyl, pentyl, hexyl and the isomeric forms thereof.

Examples of an aryl portion of from six to ten carbon atoms inclusive are phenyl, naphthyl and benzyl.

Examples of cycloalkyl of from three to seven carbon atoms, inclusive are cyclopropyl, cyclobutyl, cyclohexyl, cyclopentyl, and cycloheptyl.

Examples of alkoxy of from one to six carbon atoms inclusive are methoxy, ethoxy, propoxy, butoxy, pentoxy, and hexoxy and the isomeric forms thereof.

Examples of halogen, are chlorine, bromine and fluorine.

Pharmacologically acceptable metal ions are those metal ions such as $Ca^{++}Zn^{++}$, $Mg^{++}$, $Al^{+++}$, $Fe^{++}$ $Fe^{+++}$ and the like. It is an intention of this invention that these metal ions can be used alone or in combination.

Pharmacologically acceptable anions, are those anions such as the halides, (chloride, bromide and fluoride) or other pharmacologically acceptable anions such as acetate, sulfate, and phosphate. It is an intention of this invention that these anions can be used alone or in combination.

Examples of suitable solvents for a liquid low calorie sweetener include, but are not limited to, ethanol, water, glycol, glycerol and suitable combinations thereof.

The chemical structure of the dipeptide sweeteners allows for the formation of a complex structure via the combination of a metal ion and the amino acid moiety of the sweetener. For example, APM could form either a five member or six member ring complex or both with a metal ion.

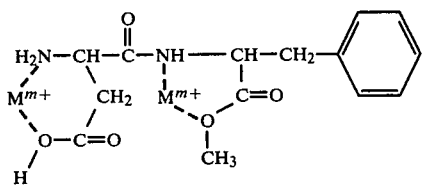

The dipeptide sweetener metal complex shows a number of properties which are tremendous improvements over the dipeptide sweeteners of the prior art. The dissolution rate of the complex is greatly improved. Thus, no additional methods or mechanical preparations are necessary to insure quick dissolution for e.g. a tabletop dipeptide sweetener. Therefore, the complexes are also extremely useful in beverage systems. They may be added to liquid beverages in the form of tablets or the like. With dry beverages they may be intermixed with other ingredients. Sugar substitutes resembling sucrose in bulk form can easily be prepared by either admixing, spraydrying or dissolving with and dehydrating known bulking agents. Because of the dipeptide metal complexes high rate of dissolution in aqueous systems they are ideal as sweetening agents in dry systems requiring rapid preparation such as beverages. The complexes will readily dissolve in room temperature water while the dipeptide sweeteners will not. A preferred embodiment of this invention is as an easily spraydried nonheat sensitive dipeptide sweetener-metal complex. In addition to increased dissolution rate and solubility in aqueous systems, the solubility in alcohol is also greatly increased. Therefore, for example, the dipeptide sweetener complex could be used to sweeten alcoholic beverages. The high concentration solution of the dipeptide-metal complex could also be used as a liquid, low-calorie sweetener. Such a liquid, low-calorie sweetener may find utility in such foodstuffs as gelatin desserts, fruit flavored beverages, cereal, cake mixes, fruit juices, syrups, salad dressings, pet foods and the like. However, it should be obvious to those skilled in the art that its utility is not restricted to the systems set forth herein and may find invaluable applicaton in cough medicines, tonics and the like. A preferred embodiment of this invention contemplates a liquid table sweetener as a replacement for sucrose and previously employed liquid sweeteners.

The following alcoholic concentrations for APM have been achieved:

| Complex | wt % APM |
|---|---|
| $Mg^{++}$—APM—$Cl_2$ | 20% |
| $Fe^{+++}$—APM—$Cl_3$ | 19% |
| $Al^{+++}$—2 APM—$Cl_3$ | 37% |

The dissolution rate is also improved, dissolving instantly, thus greatly reducing the need for mechanical agitation to produce dissolution. The thermal stability of the complexes are much higher than the dipeptide sweeteners or their salts. For example, a sample of APM or APM HCl heated for 20 minutes at 170° C. discolors and is devoid of sweet taste. A metal complex consisting of a 1:1 calcium APM complex retains its original color, appearance and sweet taste. This is extremely useful for baking, for instance, and will lead to an extended shelf life for such artificially sweetened products. The dipeptide metal complex sweeteners of this invention may be, for example, prepared by mixing and co-grinding the dipeptide sweetener with a metal halide and then reacting them in an organic solvent such as ethanol. The complexes may also be formed in situ, for example during baking where the ingredients are present in the baking materials. $Ca^{++}$ could for instance be obtained from dairy products and the like and the free base APM present. The organic solvent may be removed by evaporation. It is also possible that crystal or residue organic solvent remains in the complex crystal structure and could be essential in the desired improved physical properties. To obtain a high concentration complex in an alcohol solution, the alcohol solution is filtered instead of evaporated. The ratio of metal to dipeptide sweetener that produces optimum results may be systematically determined but, in general, the ratio of dipeptide sweetener to metal ion will be from about 0.5 to 2. As is generally accepted practice for complex formation the sweetener may be solubilized and stabilized by an appropriate metal-anion. The amount of hydration if any, will depend on the individual complex. But for example the molecular structure of the $Ca^{++}$-APM-$Cl_2$ complex is determined to be.

$$APM \cdot Ca^{++} \cdot 2Cl^- \cdot C_2H_5OH \cdot H_2O$$

It has been found also that certain hybrid complexes of the sweeteners exhibit better dissolution rate or solubility than the pure sweetener metal complex. A hybrid sweetener complex is a complex mixture where two or more metal ions, two or more anions, or both are used. The use of the APM-metal complex in alkaline pH drinks, such as coffee, and tea with or without cream can result in some degree of precipitation. It was found that the formation of precipitates in such alkaline solutions can be entirely prevented by adding from 0.5% to 10% of disodium edetate (EDTA) or other pharmacologically acceptable strong chelating agent to the APM-metal complex.

The invention will appear more fully from the examples which follow. These examples are given by way of illustration only and are not to be construed as limiting the invention either in spirit or in scope as many modifications both in materials and methods will be apparent from this disclosure to those skilled in the art.

DESCRIPTION OF THE PREFERRED EMBODIMENTS

Example 1 APM-calcium complex, 1:1

A 1:1 APM-calcium complex is prepared by mixing and co-grinding 20.0 g of APM and 10.0 g of CaCl$_2$ 2H$_2$O. About 150 ml dehydrated USP alcohol is added and the mixture is stirred vigorously for about one minute. The mixture changes to a viscous mass which is sprayed on aluminum pans and dried in vacuum oven for two hours at 90° C. The dried material is ground to a fine white powder.

Example 2 APM-Magnesium complex, 1:1-alcohol solution

A high concentration solution of an APM-magnesium complex in 1:1 ratio is prepared by mixing and co-grinding 20.0 g of APM and 7.3 g of MgCl$_2$ (98% pure). About 100 ml of ethanol is added and the mixture is stirred for ten minutes and then filtered.

Example 3 APM-Iron(III) complex, 1:1-alcohol solution

A high concentration solution of an APM-iron (III) complex in a 1:1 ratio is obtained according to the procedure of Example 3 by using 11.0 g of FeCl$_3$ and 20.0 g of APM.

Example 4 High concentration APM-Ca$^{++}$ complex, aqueous

A high concentration aqueous solution of APM-Ca-complex is prepared by first forming a slurry of 6.0 g of APM in 100 ml of distilled water. A total of 43 g of CaCl$_2$.2H$_2$O is added in five portions with vigorous stirring. Optionally the pH of the solution is adjusted to 4.5 using a 10% NaOH solution. The solution is then filtered.

Example 5 APM-Zn$^{++}$ complex, 1:1

Co-grind 20.0 g APM and 9.26 g ZnCl$_2$ to a fine powder. 150 ml ethanol is added and stirred vigorously. The reacton occurs in about one minute which takes up most of the alcohol. The mixture is spread on an aluminum pan and dried under vacuum and heated to 90° C. for two hours.

Example 6 2APM-Ca$^{++}$-Zn$^{++}$ hybrid complex

Co-grind 20.0 g APM, 4.63 g ZnCl$_2$ anhydrous, and 5.0 g CaCl$_2$ 2H$_2$O to a fine powder. About 70 ml of ethanol is added. Mix well and grind for ten minutes to a homogenous mixture. The mixture is spread on an aluminum pan and dried at 90° C. under vacuum for two hours.

Example 7 APM Al$^{+++}$ complex 2:1-alcohol solution

Co-grind 20.0 g APM and 8.2 g AlCl$_3$ 6H$_2$O to fine powder. Add 30 ml ethanol. Mix and grind the remaining solids until they are near to complete dissolution. Let solution settle, then filter.

Example 8 APM-Ca$^{++}$ complex with EDTA

To a 240 ml cup of coffee is added 57 mg of the APM-Ca$^{++}$ complex. A small percipitate of Ca(OH)$_2$ forms. The percipitate is completely redissolved upon addition of 5 mg of EDTA. 5 mg of EDTA mixed with 57 mg of the APM-Ca$^{++}$ complex results in a sweetener which dissolves readily in 240 ml of coffee with no percipitate formed.

What I claim is:

1. A dipeptide sweetener-metal complex of the formula:

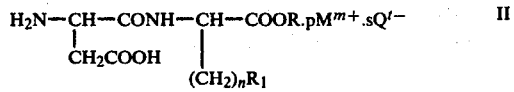

wherein the stereochemical configuration is:

DL-DL, DL-L, L-DL or L L wherein R is:
(a) alkyl of from one to six carbon atoms;
(b) alkylaryl, the alkyl portion of from one to six carbon atoms, inclusive, the aryl portion of from six to ten carbon atoms, inclusive; or
(c) cycloalkyl of from three to seven carbon atoms, inclusive;

wherein R$_1$ is:
(a) alkyl of one to six carbon atoms, inclusive;
(b) a saturated, unsaturated, or partially saturated six carbon ring, which may be optionally substituted by R$_2$;

wherein R$_2$ is:
(a) hydroxy;
(b) alkoxy of one to six carbon atoms, inclusive;
(c) alkyl of one to six carbon atoms, inclusive;
(d) halogen; or
(e) —S(O)$_f$(CH$_2$)$_k$(CH$_3$) wherein f is 0, 1 or 2; wherein k is an integer of from 0 to 5, with the proviso that n is 1 or 2;

wherein n is an integer of from zero to 5 wherein m and t are integers of from one to three either the same or different;

wherein p is the M$^{m+}$/dipeptide sweetener ratio which may be from 0.1 to 3;

wherein s is the ratio of Q$^{t-}$ to the dipeptide sweetener and wherein p×m=s×t;

wherein M$^{m+}$ is a pharmacologically acceptable Metal ion or a combination of pharmacologically acceptable Metal ions;

wherein Q$^{t-}$ is a pharmacologically acceptable anion, or a combination of pharmacologically acceptable anions;

wherein the dipeptide sweetener-metal complex may either by hydrated or unhydrated.

2. A complex according to claim 1 wherein M$^{m+}$ is a combination of pharmacologically acceptable Metal ions.

3. APM-Ca$^{++}$Zn$^{++}$ mixed ion complex, according to claim 2.

4. A complex according to claim 1 wherein M$^{m+}$ is pharmacologically acceptable Metal ion.

5. A complex according to claim 4 wherein Q is Cl.

6. A complex according to claim 5 wherein the dipeptide sweetener portion of the complex is APM.

7. APM-Ca$^{++}$ complex, according to claim 6.

8. APM-Fe$^{+++}$ complex, according to claim 6.

9. APM-Mg$^{++}$ complex, according to claim 6.

10. APM-Al$^{+++}$ complex, according to claim 6.

11. APM-Zn$^{++}$ complex, according to claim 6.

12. A composition consisting of a dipeptide sweetener-metal complex of claim 1 and 0.5% to 10% of a pharmacologically acceptable strong chelating agent.

13. A composition according to claim 12 wherein the chelating agent is from 5% to 10% of the weight of the dipeptide sweetener-metal complex.

14. A composition according to claim 13 wherein the chelating agent is EDTA disodium salt.

15. A liquid low-calorie sweetener composition comprising a dipeptide sweetener-metal complex of the formula:

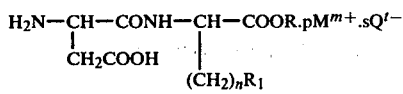

wherein the stereochemical configuration is:

DL-DL, DL-L, L-DL or L-L wherein R is:
(a) alkyl of from one to six carbon atoms;
(b) alkylaryl, the alkyl portion of from one to six carbon atoms, inclusive, the aryl portion of from six to ten carbon atoms, inclusive; or
(c) cycloalkyl of from three to seven carbon atoms, inclusive;

wherein R$_1$ is:
(a) alkyl of one to six carbon atoms, inclusive; or
(b) a saturated, unsaturated, or partially saturated 6 carbon ring, which may be optionally substituted by R$_2$;

wherein R$_2$ is:
(a) hydroxy;
(b) alkoxy of one to six carbon atoms, inclusive;
(c) alkyl of one to six carbon atoms, inclusive;
(d) halogen; or
(e) —S(O)$_f$(CH$_2$)$_k$(CH$_3$) wherein f is 0, 1 or 2; wherein p is an integer of from 0 to 5, with the proviso that n is 1 or 2;

wherein n is an integer of from zero to five;

wherein m and t are integers of from one to three;

wherein p is the M$^{m+}$/sweetener ratio which may be from 0.1 to 3;

wherein s is the ratio of Q$^{t-}$ to the dipeptide sweetener and wherein p×m=s×t;

wherein M$^{m+}$ is a pharmacologically acceptable Metal ion or a combination of pharmacologically acceptable Metal ions;

wherein Q$^{t-}$ is a pharmacologically acceptable anion or a combination of pharmacologically acceptable anions;

wherein the dipeptide sweetener-metal complex may either be hydrated or unhydrated; and wherein the dipeptide sweetener-metal complex is dissolved in a consumable solvent or combination of solvents in a concentration up to about 40% to make a high concentration liquid low-calorie sweetener.

16. A liquid low-calorie sweetener, according to claim 15 wherein the solvent is ethanol.

17. A liquid low-calorie sweetener of claim 16 wherein the dipeptide sweetener portion of the complex is APM.

18. A high concentration ethanolic solution of APM-Mg$^{++}$ complex, a composition according to claim 17.

19. A high concentration ethanolic solution of APM-Fe$^{+++}$ complex, a compound according to claim 17.

20. A high concentration ethanolic solution of APM-Al$^{+++}$ complex, a compound according to claim 17.

21. A liquid low-calorie sweetener, according to claim 15 wherein the solvent is water.

* * * * *